United States Patent

Benson et al.

Patent Number: 5,811,604
Date of Patent: Sep. 22, 1998

[54] CONTINUOUS PRODUCTION OF 1,1,1,3,3,3-HEXAFLUOROPROPANE AND 1-CHLORO-1,1,3,3,3-PENTAFLUOROPROPANE

[75] Inventors: Kevin Robert Benson, West Seneca; David Elliott Bradley, Buffalo; David Nalewajek, West Seneca, all of N.Y.

[73] Assignee: AlliedSignal, Inc., Morristown, N.J.

[21] Appl. No.: 796,002

[22] Filed: Feb. 5, 1997

[51] Int. Cl.[6] .................................................. C07C 17/00
[52] U.S. Cl. ............................................................ 570/167
[58] Field of Search ............................................. 570/167

[56] References Cited

U.S. PATENT DOCUMENTS 5,395,997  3/1995  Van Der Puy et al. ................. 570/167
5,608,126  3/1997  Morikawa et al. ..................... 570/167
5,608,127  3/1997  Gumprecht ............................. 570/170

*Primary Examiner*—Jane Fan
*Assistant Examiner*—Garth M. Dahlen
*Attorney, Agent, or Firm*—Jay P. Friedenson

[57] ABSTRACT

A process for the continuous production of 1,1,1,3,3,3-hexafluoropropane (HFC-236fa) and/or 1-chloro-1,1,3,3,3-pentafluoropropane (HCFC-235fa) in the liquid phase wherein the HFC-235fa and/or HFC-236fa serve as solvents for the reaction. When the reaction is conducted in the presence of a catalyst of $SbF_3$, $SbF_5$ or a mixture of $SbF_5$ and $HSO_3F$, the reaction mass is unexpectedly less corrosive to the reaction vessel used.

23 Claims, 1 Drawing Sheet

CONTINUOUS PRODUCTION OF 1,1,1,3,3,3-HEXAFLUOROPROPANE AND 1-CHLORO-1,1,3,3,3-PENTAFLUOROPROPANE

BACKGROUND OF THE INVENTION

1. Field of the Invention

The present invention relates to the preparation of halocarbons. More particularly, the invention pertains to the continuous production of 1,1,1,3,3,3-hexafluoropropane (HFC-236fa) and/or 1-chloro-1,1,3,3,3-pentafluoropropane (HCFC-235fa) in the liquid phase wherein the HFC-235fa and/or HFC-236fa serve as solvents for the reaction. When the reaction is conducted in the presence of certain fluorination catalysts the reaction mass is unexpectedly less corrosive to the reaction vessel used.

2. Description of the Prior Art

In recent years there has been far-reaching concern that certain highly chlorinated hydrochlorocarbons and hydrochlorofluorocarbons might be detrimental to the Earth's ozone layer. As a result, there is a worldwide effort to use halocarbons which contain fewer chlorine substituents. In this regard HFC-236fa is a hydrofluorocarbon has a zero ozone depletion potential. HFC-236fa is known from U.S. Pat. No. 5,395,997 which is incorporated herein by reference. However, it has been a problem in the art to conduct an economical process for the continuous preparation of HFC-236fa. The production of hydrofluorocarbons, i.e. compounds containing only carbon, hydrogen and fluorine, has been the subject of increasing interest to provide environmentally desirable products for use as solvents, foam blowing agents, refrigerants, cleaning agents, aerosol propellants, heat transfer media, dielectrics, fire extinguishing compositions and power cycle working fluids. It is known in the art to produce hydrofluorocarbons (HFCs) by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are non-ozone depleting, but they are also non-flammable and non-toxic as compared to the chlorine containing compounds.

It has now been found that HFC-236fa as well as HCFC-235fa may be continuously and economically produced in a continuous process by the liquid phase reaction of 1,1,1,3,3,3-hexachloropropane, HCC-230, with hydrogen fluoride in the presence of certain fluorination catalysts wherein the reaction products themselves serve as solvents for the reaction. By this method, HFC-235fa and HFC-236fa can be prepared using a much smaller than expected amount of catalyst compared to the known $SbCl_5$ and $SbCl_3F_2$ catalytic systems that require high concentrations of the antimony compounds to function correctly. It is theorized that the lower Lewis acidity, as measured by the Hammet scale of the $SbCl_5$ derived catalyst requires a higher concentration to achieve the same superacid activity as is achieved by much smaller concentrations of $SbF_5$. As a result, the prior art problems of corrosion of typical metal alloy reaction vessels is much improved by this invention even when high pressures are used. The ability to use metal alloy reactors is of considerable benefit to the manufacturer of HFC-236fa/HFC-235fa for a number of reasons.

The reactors which use the catalyst system employing the present lower amount of $SbF_5$ are considerably less corroded than would have occurred with the high $SbCl_5$ concentration system. The latter has been demonstrated to be very corrosive to metals. This low concentration $SbF_5$ based system would also have other advantages such as the low viscosity and use of a one liquid phase reaction mixture. In addition, the solvents/products HFC-236fa and HFC-235fa are more chemically stable with respect to their more chlorinated precursors and have a greater ability to dissolve large amounts of HF over a wide temperature range.

SUMMARY OF THE INVENTION

The invention provides a continuous process for the preparation of 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane which comprises continuously contacting a stream of 1,1,1,3,3,3-hexachloropropane with a stream of hydrogen fluoride in the liquid phase in a reactor containing a solvent comprising 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane in the presence of a fluorination catalyst selected from the group consisting of at least one of $SbF_3$, $SbF_5$ and a mixture of $SbF_5$ and $HSO_3F$ under conditions sufficient to thereby produce 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane.

DETAILED DESCRIPTION OF THE PREFERRED EMBODIMENT

Figure 1:
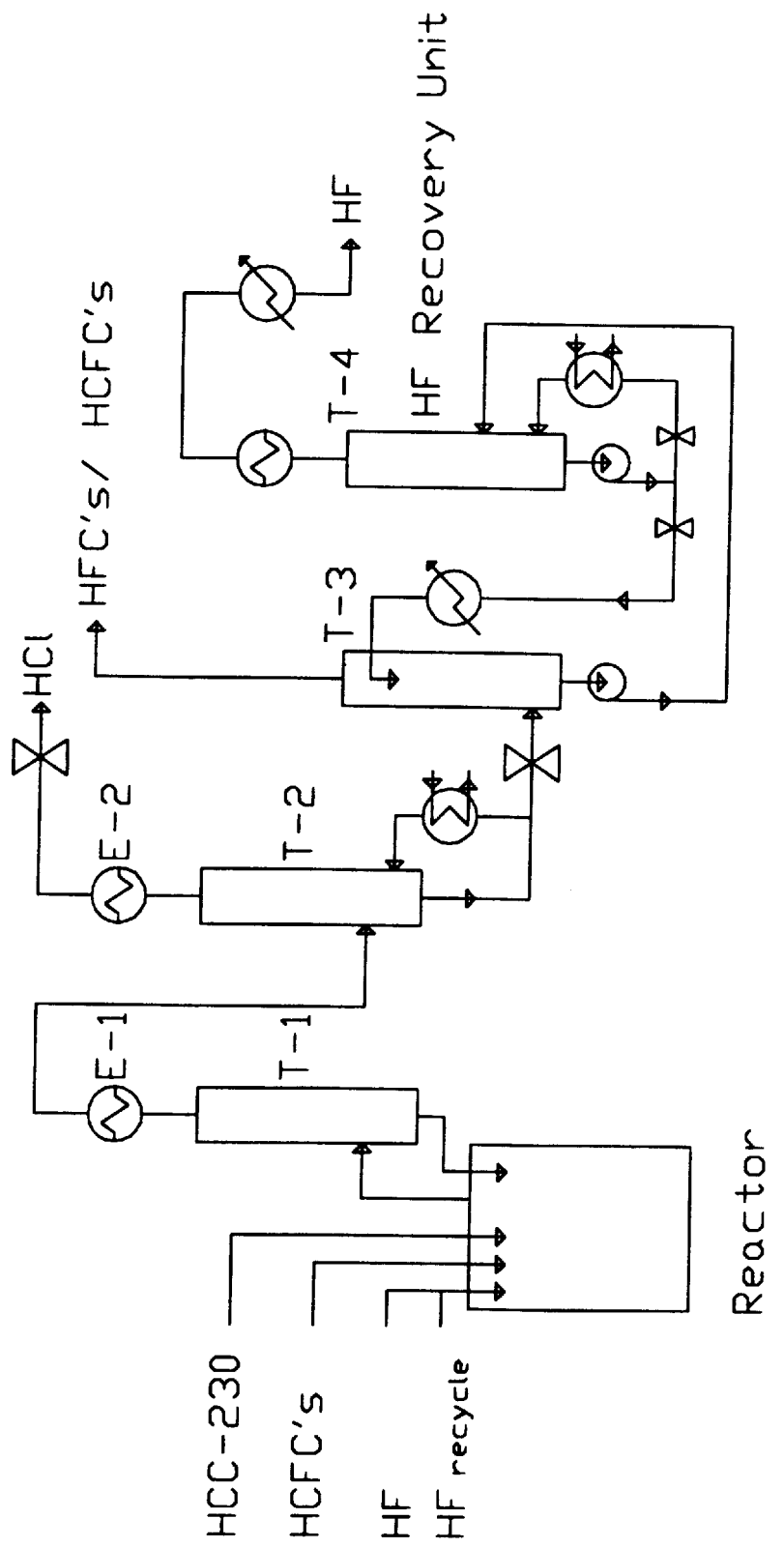
FIG. 1 shows a simplified process flow schematic diagram of an apparatus useful for carrying out the invention.

The invention generally provides for the continuous catalytic, liquid phase fluorination of HCC-230 with HF to HFC-236fa and/or HCFC-235fa wherein HFC-235fa and/or HFC-236fa serve as solvents for the reaction. In the practice of the present invention, a liquid phase catalyst as described below is charged into a fluorination reactor prior to heating the reactor. The reactor according to this invention may be any suitable fluorination reaction pressure vessel or autoclave but it should be constructed from materials which are resistant to the corrosive effects of hydrogen fluoride such as Hastalloy, Inconel, Monel and fluoropolymer-lined vessels. Then the HCC-230 to be fluorinated and HF are simultaneously fed to the reactor after the reactor reaches the desired temperature.

Liquid phase catalysts useful for this invention are at least one of $SbF_3$, $SbF_5$ and a mixture of $SbF_5$ and $HSO_3F$. The catalyst may be charged to a fluorination reactor prior to heating of the reactor. Thereafter the HCC-230 and HF are simultaneously fed to the reactor after the reactor reaches the desired temperature. The HCC-230 and HF may be fed to the reactor at any convenient temperature and pressure. The reactor is run at a preferred temperature ranging from about 60° C. to about 120° C.; more preferably from about 70° C. to about 110° C. and most preferably from about 80° C. to about 100° C. Reactor pressure is preferably maintained at from about 85 to about 500 psig; more preferably from about 120 to about 400 psig and most preferably from about 150 to about 300 psig. The most desired product is HFC-236fa. In order to optimize the yield of HFC-236fa, the HF to HCC-230 mole ratio is set to range from about 5:1 to about 7:1; more preferably from about 5.5:1 to about 6.5:1 and most preferably from about 5.9:1 to about 6.1. If the HF to HCC-230 mole ratio is set to less than 5:1, such as from about 3:1 to about 5:1, then more HCFC-235fa results. At 5:1 an approximately 50:50 mixture of HFC-236fa and HCFC-235fa is obtained.

The amount of catalyst is that amount effective to convert HCC-230 to HFC-236fa and/or HCFC-235fa. The amount of catalyst preferably ranges from about 0.5% to about 10%, more preferably from about 1% to about 5%, and most preferably from about 2% to about 4% based on the total weight of reactor contents. The reaction is conducted in a solvent which comprises HFC-236fa, HCFC-235fa or a mixture of HFC-236fa and HCFC-235fa. The amount of solvent in the total reaction mass preferably ranges from about 40% to about 80%, more preferably from about 50% to about 70%, and most preferably from about 55% to about 65% based on the total weight of reactor contents. In the preferred embodiment, the foregoing amount of solvent is put into the reaction vessel at startup and maintained by removal of the solvent as it is generated by the reaction. In the preferred embodiment the feed rates of the reactants and removal rate of the reaction product are controlled such that the amount of solvent in the reaction mass remains essentially constant. In the preferred embodiment, the feed rate of the total reactant volume ranges from about 0.1 to about 10 lbs/gallon hour based on the total volume of liquids in the reactor. A more preferred range is from about 1 to about 6 lbs/gallon hour and most preferably from about 2 to about 4 lbs/gallon hour.

In the preferred embodiment, unreacted HF, HCC-230 and partially fluorinated intermediates are recycled back to the reactor for further fluorination. The HFC-235fa and HFC-236fa are then separated from the reaction mass. Separation may be conducted by known separation techniques such as extraction and distillation. This may be done using a standard distillation column in a method well known to one skilled in the art.

The continuous production arrangement can utilize several feature of existing liquid phase HF reaction processes, including a pressure rated reactor connected to a continuous fractional distillation system. A process flow schematic diagram is shown in FIG. 1. In this process, the reactor is maintained at a constant level volume by matching the flows of inputs and outputs from the reactor. The inputs include HCC-230, HFC-236fa/HCFC-235fa, new and recycled HF, recycled partially fluorinated organics, desiccants (for example $COCl_2$ or $SOCl_2$) and possibly trace amounts of oxidants ($Cl_2$, ClF, $ClF_3$ and/or $F_2$). The reactor outputs consist of the pressurized vapor stream leading to fractional distillation column T-1, and are composed of by-product HCl, partially fluorinated compounds, HFC-236fa/HF azeotrope, HCFC-235fa/HF azeotrope, HF, trace amounts of $SO_2/CO_2$ and possibly mists containing the reactor solution.

The reaction process would start by feeding a carefully maintained ratio of HCC-230 (with any required dehydrant dissolved in this liquid) and HF into the heated refluxing mixture of HFC-236fa/HCFC-235fa, HF and catalyst which is the superacid ($[H_2F(+)][SbF_6(-)]$ and/or $[H_2F(+)][SbF_5-SO_3F(-)]$). The rapidly formed HCl as well as additional desired products are allowed to pass through the partial condenser E-1 by maintaining the proper flow rate/temperature of coolant into E-1, while at the same time condensing sufficient amounts of the HFC-236fa/HCFC-235fa/HF as column reflux. This liquid reflux is used to condense the higher boiling partly fluorinated materials, as well as to prevent the escape of any catalyst contained in a mist in the vapor stream entering column T-1. The vapor stream passing through E-1 is fed into fractional distillation column T-2, where the HCl is separated from the desired HF-azeotrope(s) of HFC-236fa and/or HCFC-235fa. The more volatile HCl is refluxed in column T-2 with cooling provided to partial condenser E-2; the purified, uncondensed HCl is vented from the process to neutralization or HCl recovery units. The higher boiling liquid materials that accumulate in the reboiler of column T-2 are then fed at carefully maintained rates to the HF extraction column T-3. The columns T-1 and T-2 are operated at the same pressure as the reactor, while the column T-3, a counter-current vapor-liquid scrubber, is kept at near atmospheric pressure. The HF extraction fluid (such as 50 to 70 wt% HF in $H_2O$, $HSO_3F$ or $H_2SO_4$) is maintained at a temperature sufficient to allow the IFC-236fa and/or HCFC-235fa to leave the top of the extractor as vapors. The HF-depleted extraction fluid is fed to the top of T-3, and withdrawn as an HF-enriched liquid. This liquid is then processed to recover the HF via techniques such as distillation. This recovered HF (also containing small amounts of organic products/intermediates) is then recycled back to the reactor. The organic vapors exiting from the extractor column T-3 are then purified via well-known neutralization and distillation techniques. A portion of the anhydrous vapor leaving T-3 may also be condensed and also recycled back to the reactor to maintain the proper amount of HFC-236fa/HFC-235fa in the reactor, should this be necessary.

The process herein described is capable of achieving a conversion of HCC-230 into HFC-235fa and/or HFC-236fa at a conversion rate of at least about 99% and at yields of at least about 95% of HFC-235fa and/or HFC-236fa.

The catalyst can also be reused frequently, with occasional reoxidation when required. If the catalytic activity of the $SbF_5$ needs to be increased, a regulated amount of $HSO_3F$ and/or $SO_3$ can be added to the HFC-236fa/$SbF_5$ solution. Such a system is up to 100 times more "acidic" than the corresponding $SbF_5$-HF system, which in turn is 100 times more acidic than the $SbCl_5$-HF based system. In addition to the greater acidity, the acids are in a highly solvated form, and apparently less likely to aid in the oxidation/corrosion of metals such as nickel.

The following non-limiting examples serve to illustrate the invention.

EXAMPLE 1

Liquid phase conversion of HCC-230 to HFC-236fa Using $SbF_5$ and HFC-236fa as solvent.

Into a 600 mL Hastolloy autoclave was charged 6.4 g (0.03 mol) of $SbF_5$, 60 g (3.0 mol) of HF, 101 g (0.66 mol) of HFC-236fa and 62.8 g (0.25 mol) of HCC-230. The mixture is heated to 120° C. while maintaining the internal pressure at 350 psi. After 0.5 hr., the reaction is complete. The excess HF is removed from the reaction product by passing the crude material through a potassium hydroxide scrubber. Yield of isolated product is 199.4 g (99%) of HFC-236fa which contained 5% of HCFC-235 which can be recycled through the process to produce additional HFC-236fa. The overall selectivity of the process is 95% with a conversion of 100% of the HCC-230.

EXAMPLE 2

Liquid phase conversion of HCC-230 to HFC-236fa Using $SbF_3$ and HFC-236fa as solvent.

Into a 600 mL Hastolloy autoclave is charged 0.03 mol of $SbF_3$, 3.0 mol of HF, 0.66 mol of HFC-236fa and 0.25 mol of HCC-230. The mixture is heated to 120° C. while maintaining the internal pressure at 350 psi. After 0.5 hr., the reaction is complete. The excess HF is removed from the reaction product by passing the crude material through a potassium hydroxide scrubber. Results similar to those of Example 1 are obtained.

EXAMPLE 3

Liquid Phase conversion of HCC-230 to HFC-236fa Using $SbF_5$ and $HSO_3F$ as co-catalyst.

The reactant charges and conditions are the same as those described in Example 1 with the exception that 0.03 mol of $HSO_3F$ was added as a co-catalyst. After 0.5 hour, the reaction contents are isolated as described above to yield HFC-236fa. Similar results are observed. In this experiment, some reactor pitting occurs.

What is claimed is:

1. A continuous process for the preparation of 1,1,1 3,3,3-hexafluoropropane; 1-chloro-1,1,3,3,3,-pentafluoropropane or a mixture of 1,1,1,3,3,3-hexafluoropropane and 1-chloro-1,1,3,3,3-pentafluoropropane which comprises continuously contacting a stream of 1,1,1,3,3,3-hexachloropropane with a stream of hydrogen fluoride in the liquid phase in a reactor containing a solvent comprising 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane in the presence of a fluorination catalyst selected from the group consisting of at least one of $SbF_3$, $SbF_5$ and a mixture of $SbF_5$ and $HSO_3F$ under conditions sufficient to thereby produce 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane wherein the solvent to catalyst molar ratio is at least 5.6.

2. The process of claim 1 wherein said catalyst comprises $SbF_3$.

3. The process of claim 1 wherein said catalyst comprises $SbF_5$.

4. The process of claim 1 wherein said catalyst comprises a mixture of $SbF_5$ and $HSO_3F$.

5. The process of claim 1 wherein said contacting is conducted at from about 60° C. to about 120° C.

6. The process of claim 1 wherein said contacting is conducted at a pressure of from about 85 psig to about 500 psig.

7. The process of claim 1 wherein the feed rate of the total reactant volume ranges from about 0.1 to about 10 lbs/gallon hour based on the total volume of liquids in the reactor.

8. The process of claim 1 wherein the HF to HCC-230 mole ratio ranges from about 5:1 to about 7:1.

9. The process of claim 1 wherein the HF to HCC-230 mole ratio ranges from about 3:1 to about 5:1.

10. The process of claim 1 wherein the amount of catalyst ranges from about 0.5% to about 10% based on the total weight of reactor contents.

11. The process of claim 1 wherein 1-chloro-1,1,3,3,3-pentafluoropropane is produced.

12. The process of claim 1 wherein 1,1,1,3,3,3-hexafluoropropane is produced.

13. The process of claim 1 wherein a mixture of 1-chloro-1,1,3,3,3-pentafluoropropane and 1,1,1,3,3,3-hexafluoropropane is produced.

14. The process of claim 1 wherein the contacting is conducted in a solvent which comprises 1,1,1,3,3,3-hexafluoropropane and 1,1,1,3,3,3-hexafluoropropane is produced.

15. The process of claim 1 wherein the contacting is conducted in a solvent which comprises 1-chloro-1,1,3,3,3-pentafluoropropane and 1-chloro-1,1,3,3,3-pentafluoropropane is produced.

16. The process of claim 1 wherein the contacting is conducted in a solvent which comprises a mixture of 1,1,1,3,3,3-hexafluoropropane and 1-chloro-1,1,3,3,3-pentafluoropropane and a mixture of 1,1,1,3,3,3-hexafluoropropane and 1-chloro-1,1,3,3,3-pentafluoropropane is produced.

17. The process of claim 1 wherein the amount of solvent in the total reaction mass ranges from about 40% to about 80% based on the total weight of reactor contents.

18. The process of claim 1 further comprising the additional step of subsequently separating 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane from other components in the reaction.

19. The process of claim 16 wherein the separating is conducted by distillation.

20. The process of claim 1 further comprising subsequently recycling any unreacted hydrogen fluoride, 1,1,3,3,3-hexafluoropropane and by-products in the reaction product back to the reactor.

21. The process of claim 1 wherein the feed of hydrogen fluoride and 1,1,1,3,3,3-hexachloropropane are controlled to maintain a constant amount of reaction solvent.

22. The process of claim 1 wherein the conversion of 1,1,1,1,3,3-hexachloropropane into 1,1,1,3,3,3-hexafluoropropane; 1-chloro-1,1,3,3,3-pentafluoropropane or a mixture of 1,1,1,3,3,3-hexafluoropropane and 1-chloro1,1,3,3,3-pentafluoropropane is at least about 99%.

23. A process for the preparation of 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane which comprises continuously contacting a stream of 1,1,1,3,3,3-hexachloropropane with a stream of hydrogen fluoride in a liquid phase reactor containing a solvent comprising 1,1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane in the presence of a catalyst comprising a mixture of $SbF_5$ and $HSO_3F$ under conditions sufficient to thereby produce 1, 1,1,3,3,3-hexafluoropropane; 1-chloro-1,1,3,3,3-pentafluoropropane or a mixture of 1,1,1,3,3,3-hexafluoropropane and 1-chloro-1,1,3,3,3-pentafluoropropane wherein the solvent to catalyst molar ratio is at least 5.6.

* * * * *